(12) United States Patent
Nakano et al.

(10) Patent No.: US 7,951,877 B2
(45) Date of Patent: May 31, 2011

(54) PROCESS FOR THE PRODUCTION OF VINYL COMPOUND

(75) Inventors: Jun Nakano, Tokyo (JP); Takeru Horino, Tokyo (JP); Makoto Miyamoto, Tokyo (JP); Atsushi Hirashima, Tokyo (JP); Yasumasa Norisue, Tokyo (JP)

(73) Assignee: Mitaubishi Gas Chemical Company, Inc., Tokyo (JP)

( * ) Notice: Subject to any disclaimer, the term of this patent is extended or adjusted under 35 U.S.C. 154(b) by 327 days.

(21) Appl. No.: 12/213,237

(22) Filed: Jun. 17, 2008

(65) Prior Publication Data

US 2009/0012331 A1 Jan. 8, 2009

(30) Foreign Application Priority Data

Jun. 18, 2007 (JP) .................. 2007-160539

(51) Int. Cl.
  C08G 65/48 (2006.01)
  C08F 290/06 (2006.01)
  C07C 43/20 (2006.01)
(52) U.S. Cl. ........ 525/392; 568/636; 568/637; 568/640; 568/641; 568/643; 568/644; 568/645; 568/646; 568/658
(58) Field of Classification Search .............. None
  See application file for complete search history.

(56) References Cited

U.S. PATENT DOCUMENTS 7,193,019 B2 * 3/2007 Norisue et al. ............... 525/392

FOREIGN PATENT DOCUMENTS

EP 0 310 835 4/1989
EP 1 526 148 4/2005

* cited by examiner

Primary Examiner — Rosalynd Keys
(74) Attorney, Agent, or Firm — Wenderoth, Lind & Ponack, L.L.P.

(57) ABSTRACT

A process, advantageous in producibility, for the production of a vinyl compound containing very small amounts of ionic impurities and hydrolysable halogens, which is capable of curing by means of heat and/or light and giving a cured product having excellent dielectric characteristics and heat resistance, which process can efficiently remove a generated salt and comprises reacting a non-protonic polar solvent solution of a specific bifunctional phenylene ether oligomer with a vinylbenzyl halide in the presence of an alkoxide of an alkali metal,
  wherein the thus-obtained reaction solution is acidified with a specific amount of an acidic substance, then a salt generated is removed, an alkali substance containing a specific amount of an alkali metal is added to the thus-obtained solution, then a salt generated is removed, and the thus-obtained solution is mixed with water or a water-alcohol mixed solution, to precipitate a solid.

9 Claims, 3 Drawing Sheets

PROCESS FOR THE PRODUCTION OF VINYL COMPOUND

FIELD OF THE INVENTION

The present invention relates to a process for the production of a vinyl compound obtained by reacting a bifunctional phenylene ether oligomer with a vinylbenzyl halide. More specifically, it relates to an industrially-advantageous process for the production of a vinyl compound containing very extremely small amounts of ionic impurities, in which a salt generated in a reaction is particularly easily removed.

BACKGROUND OF THE INVENTION

The present inventors have found that vinyl compounds excellent in curability, dielectric characteristics and heat resistance are obtained by introducing vinyl groups into terminals of bifunctional phenylene ether oligomers which inherit excellent dielectric characteristics and heat resistance from polyphenylene ether resins (see JP-A-2004-59644 and JP-A-2004-67727). The present inventors have also found industrially-advantageous processes of producing the above vinyl compounds in which the content of ionic impurities is extremely small (see JP-A-2005-126523 and JP-A-2006-28111). However, in these processes, it takes a long period of time to remove a salt generated in the step of synthesis so that there is a problem about poor producibility.

SUMMARY OF THE INVENTION

Under the above circumstances, it is an object of the present invention to provide a process, advantageous in producibility, for the production of a vinyl compound which is capable of curing by means of heat and/or light and giving a cured product having excellent dielectric characteristics and heat resistance, wherein a salt generated can be efficiently removed and the contents of ionic impurities and hydrolysable halogens are small.

The present inventors have made diligent studies on processes of producing vinyl compounds for attaining the above object and as a result found the following. That is, when a reaction solution after the reaction between a bifunctional phenylene ether oligomer and a vinylbenzyl halide is acidified with an acidic substance in an excess amount, the particle diameter of a salt generated increases and therefore the sedimentation velocity thereof remarkably increases, so that it is possible to shorten a period of time required for the removal of the salt largely. However, when the reaction solution is acidified with the acidic substance in an excess amount for facilitating the removal of the salt, a new problem is that a large amount of a hydrolysable halogen remains in a vinyl compound obtained.

The present inventors have made further studies and as a result found that the content of a hydrolysable halogen can be decreased by adding an alkali substance to the acidic solution, from which the salt has been removed, obtained by the above method and thereby generating a salt between the alkali substance and the acidic substance. On the basis of the above finding, the present inventors have completed the present invention.

According to the present invention, there is provided a process for the production of a vinyl compound represented by formula (1), comprising subjecting a non-protonic polar solvent solution of a bifunctional phenylene ether oligomer represented by formula (2) to the steps of:

1) reacting the bifunctional phenylene ether oligomer of formula (2) with a vinylbenzyl halide in the presence of an alkoxide of an alkali metal in an amount in excess of the number of moles of the vinylbenzyl halide, to synthesize the vinyl compound represented by formula (1), 2) after the completion of the reaction, adding an acidic substance in such an amount that the number (B) of moles of the acidic substance is at least 1.0 molar times as much as a difference (A) between the number of moles of the alkali metal of the alkoxide and the number of moles of the vinylbenzyl halide, to obtain a solution (a) and removing a salt precipitated in the solution (a) by filtration, 3) adding an alkali substance containing an alkali metal in such an amount that the number (C) of moles of the alkali metal satisfies C/(xB-A)=0.1 to 3, wherein x represents a valence of the acidic substance, to obtain a solution (b) and removing a salt precipitated in the solution (b) by filtration, to obtain a filtrate, and

4) mixing the filtrate with water or a mixed solution containing water and an alcohol, thereby precipitating the vinyl compound represented by formula (1),

—CH$_2$—$\{$O—Y$\}_a$—O—X—O—$\{$Y—O$\}_b$—CH$_2$—    (1)

wherein $R^1$, $R^2$, $R^3$ and $R^4$ are the same or different and represent a hydrogen atom, a halogen atom, an alkyl group or a phenyl group, —(O—X—O)— represents a moiety of formula (3) or formula (4), —(Y—O)— represents an arrangement of a moiety of formula (5) or an arbitrary arrangement of at least two kinds of moieties of formula (5), and each of a and b is an integer of 0 to 30, provided that at least one of a and b is not 0,

H—$\{$O—Y$\}_a$—O—X—O—$\{$Y—O$\}_b$—H   (2)

wherein —(O—X—O)— is a moiety of formula (3) or formula (4), —(Y—O)— represents an arrangement of a moiety of formula (5) or an arbitrary arrangement of at least two kinds of moieties of formula (5) and each of a and b is an integer of 0 to 30, provided that at least one of a and b is not 0,

=

(3)

wherein $R^5$, $R^6$, $R^7$, $R^{11}$ and $R^{12}$ are the same or different and represent a halogen atom, an alkyl group having 6 or less carbon atoms or a phenyl group and $R^8$, $R^9$ and $R^{10}$ are the same or different and represent a hydrogen atom, a halogen atom, an alkyl group having 6 or less carbon atoms or a phenyl group, (4)

wherein $R^{13}$, $R^{14}$, $R^{19}$ and $R^{20}$ are the same or different and represent a halogen atom, an alkyl group having 6 or less carbon atoms or a phenyl group, $R^{15}$, $R^{16}$, $R^{17}$ and $R^{18}$ are the same or different and represent a hydrogen atom, a halogen atom, an alkyl group having 6 or less carbon atoms or a phenyl group and -A- represents a linear, branched or cyclic hydrocarbon having 20 or less carbon atoms, (5)

wherein $R^{21}$ and $R^{22}$ are the same or different and represent a halogen atom, an alkyl group having 6 or less carbon atoms or a phenyl group and $R^{23}$ and $R^{24}$ are the same or different and represent a hydrogen atom, a halogen atom, an alkyl group having 6 or less carbon atoms or a phenyl group.

EFFECT OF THE INVENTION

Owing to the process provided by the present invention, it becomes possible to efficiently produce a vinyl compound in which the content of ionic impurities such as hydrolysable halogens and remaining alkali metal ions is extremely small. Further, a salt generated in a synthesis step can be efficiently removed in a short time in the process of the present invention so that the process of the present invention is advantageous in producibility. Furthermore, a cured product obtained by curing the above vinyl compound under heat has extremely excellent dielectric characteristics so that it is advantageously used as a high-frequency-support material in the fields of electric and electronic materials.

DETAILED DESCRIPTION OF THE INVENTION

The vinyl compound represented by formula (1) is synthesized by reacting a bifunctional phenylene ether oligomer represented by formula (2) with a vinylbenzyl halide in a non-protonic polar solvent in the presence of an alkoxide of an alkali metal. In the process of the present invention, after this reaction, an acidic substance is added in an amount which is specific with regard to an excess of the alkoxide of alkali metal, to obtain a solution (a), a salt precipitated in the solution (a) is removed by filtration, then an alkali substance containing a specific amount of an alkali metal is added to obtain a solution (b), a salt precipitated in the solution (b) is removed by filtration to obtain a filtrate, and the filtrate is mixed with water or a water/alcohol mixed solution, thereby precipitate the vinyl compound.

The bifunctional phenylene ether oligomer used in the present invention is not specially limited so long as it is represented by formula (2). It is preferably a bifunctional phenylene ether oligomer of formula (2) wherein $R^5$, $R^6$, $R^7$, $R^{11}$, $R^{12}$, $R^{13}$, $R^{14}$, $R^{19}$ and $R^{20}$ in —(O—X—O)— of formula (3) or (4) represent an alkyl group having 3 or less carbon atoms, $R^8$, $R^9$, $R^{10}$, $R^{15}$, $R^{16}$, $R^{17}$ and $R^{18}$ in —(O—X—O)— of formula (3) or (4) represent a hydrogen atom or an alkyl group having 3 or less carbon atoms, $R^{21}$ and $R^{22}$ in —(Y—O)— of formula (5) represent an alkyl group having 3 or less carbon atoms and $R^{23}$ and $R^{24}$ in —(Y—O)— of formula (5) represent a hydrogen atom or an alkyl group having 3 or less carbon atoms; particularly preferably a bifunctional phenylene ether oligomer of formula (2) wherein $R^5$, $R^6$, $R^7$, $R^{11}$, $R^{12}$, $R^{13}$, $R^{14}$, $R^{19}$ and $R^{20}$ in —(O—X—O)— of formula (3) or (4) are methyl groups and —(Y—O)— of formula (5) represents a moiety of formula (6) or formula (7) or a mixture of moieties of formula (6) and formula (7).

(6)

(7)

The bifunctional phenylene ether oligomer of formula (2) used in the present invention is produced by, for example, a method disclosed in JP-A-2004-115619 in which a bivalent phenol and a monovalent phenol are copolymerized in a reaction solvent in the presence of a catalyst. Examples of the reaction solvent include aromatic hydrocarbon solvents such as toluene, benzene and xylene, halogenated hydrocarbon solvents such as methylene chloride and chloroform, ketone solvents such as acetone and methyl ethyl ketone and alcohol solvents such as methanol, ethanol and isopropanol. As for the reaction conditions for obtaining the bifunctional phenylene ether oligomer, the reaction is generally carried out at 30 to 50° C. for about 1 to 5 hours.

The non-protonic polar solvent used in the present invention is not specially limited. The non-protonic polar solvent is preferably N,N-dimethylformamide, N,N-dimethylacetamide or N-methyl-2-pyrrolidone. The non-protonic polar solvents can be used alone or in combination. The amount of the non-protonic polar solvent to be used is not specially limited. The amount of the non-protonic polar solvent per 100 parts by weight of the bifunctional phenylene ether oligomer is preferably 100 to 2,000 parts by weight, more preferably 200 to 600 parts by weight.

The non-protonic polar solvent is added to a reaction solution in which the bifunctional phenylene ether oligomer has been synthesized and the reaction solvent of the reaction solution is replaced with the non-protonic polar solvent by distillation, thereby preparing a non-protonic polar solvent solution of the bifunctional phenylene ether oligomer. This is preferable because a vinyl-benzylating reaction can be successively carried out without isolating the bifunctional phenylene ether oligomer. In the replacement of the reaction solvent with the non-protonic polar solvent, it is preferred to use a non-protonic polar solvent of which the boiling point is higher than that of the reaction solvent used for the synthesis of the bifunctional phenylene ether oligomer. The above replacement of the solvents may be carried out under normal pressure or reduced pressure by a continuous distillation or a batch distillation. The temperature of a distiller is not specially limited. The distillation is preferably carried out at from 80° C. to 240° C. The survival rate of the bifunctional phenylene ether oligomer reaction solvent in the bifunctional phenylene ether oligomer solution after the replacement of the solvents is preferably 5 wt % or less, more preferably 2 wt % or less.

The non-protonic polar solvent solution of the bifunctional phenylene ether oligomer represented by formula (2) is subjected to a reaction with vinylbenzyl halide in the presence of an alkoxide of an alkali metal, thereby synthesizing the vinyl compound of formula (1). The reaction time for the above reaction can be freely selected. The reaction time is 30 minutes to 30 hours, preferably 1 hour to 10 hours. Further, the reaction temperature is not specially limited. The reaction temperature is 0 to 100° C., preferably 10 to 70° C.

The vinylbenzyl halide used in the present invention is not specially limited. The vinylbenzyl halide is preferably selected from o-vinylbenzyl chloride, m-vinylbenzyl chloride, p-vinylbenzyl chloride, and mixtures of at least two members of these chlorides; and o-vinylbenzyl bromide, m-vinylbenzyl bromide, p-vinylbenzyl bromide and mixtures of at least two members of these bromides. The vinylbenzyl halide can be used singly or at least two vinylbenzyl halides can be used in combination, as required. The amount of the vinylbenzyl halide used in the present invention is preferably 0.9 to 4.0 mole, more preferably 1.0 to 2.0 mole, per 1.0 mole of a phenolic hydroxyl group of the bifunctional phenylene ether oligomer. When the amount of the vinylbenzyl halide is too small, the amount of unreacted phenolic hydroxyl group residue becomes large so that a cure product decreases in dielectric characteristics. When the amount of the vinylbenzyl halide is too large, the amount of unreacted vinylbenzyl halide, which generates ionic impurities, increases.

The alkoxide of an alkali metal to be used in the present invention is not specially limited. The above alkoxide is preferably selected from lithium methoxide, sodium methoxide, potassium methoxide, lithium ethoxide, sodium ethoxide and potassium ethoxide. The alkoxide can be used singly or at least two alkoxides can be used in combination, as required. The amount of the alkali metal alkoxide used in the present invention is preferably 0.9 to 4.8 mole, more preferably 1.0 to 2.4 mole, per 1.0 mole of a phenolic hydroxyl group of the bifunctional phenylene ether oligomer and also is preferably 1.0 to 1.2 mole per 1.0 mole of the vinylbenzyl halide. The alkali metal alkoxide reacts with the vinylbenzyl halide to generate an ether compound, as shown in reaction formula (8). Therefore, it is possible to produce a vinyl compound in which the amount of remaining unreacted vinylbenzyl halide, which generates hydrolysable impurities, is extremely small by using the alkali metal alkoxide in an amount at least equimolar to the amount of the vinylbenzyl halide.

In the process of the present invention, the acidic substance is added after the completion of the synthesis reaction of the vinyl compound represented by formula (1), to obtain an acid solution. Owing to this, remaining alkali metal ions are efficiently removed. The acidic substance is selected from the group consisting of phosphoric acid, sulfuric acid, hydrochloric acid, aromatic sulfonic acid and aromatic carboxylic acid. The acidic substance may be used singly or at least two acidic substances may be used in combination. The acidic substance may be added in the form of a solution thereof in a non-protonic polar solvent. The number (B) of moles of the acidic substance to be added is not specially limited so long as it is at least 1.0 molar times as much as a difference (A) between the number of moles of the vinylbenzyl halide and the number of moles of the alkali metal of the alkoxide used for vinylbenzylating the bifunctional phenylene ether oligomer and is also sufficient for acidifying an excess alkali in the solution after the vinylbenzylating reaction. The acidic substance is preferably added in such an amount that, after 4 parts by weight of toluene and 4 parts by weight of pure water are added per 1 part by weight of the solution (a) obtained after the addition of the acidic substance and the mixture is stirred and then left to stand to separate an aqueous solution, the aqueous solution has a pH of 3.0 to 5.0, more preferably 3.5 to 5.0.

When the solution after the vinylbenzylating reaction is acidified with the acidic substance in an excess amount, the particle diameter of a salt generated increases and therefore the sedimentation velocity thereof remarkably increases, so that it becomes possible to remove the salt in a short time. On the other hand, when the amount of the acidic substance used in not enough, a salt consists of fine particles and therefore the sedimentation velocity thereof is slow, so that it takes a long time to remove the salt, which results in decease in producibility.

In the process provided by the present invention, the alkali substance containing a specific amount of an alkali metal is added to a filtrate obtained after the removal of the salt generated, thereby decreasing the content of a hydrolysable halogen. The alkali substance containing an alkali metal is selected from the group consisting of lithium methoxide, sodium methoxide, potassium methoxide, lithium ethoxide, sodium ethoxide, potassium ethoxide, lithium hydroxide, sodium hydroxide and potassium hydroxide. The alkali substance can be used singly or at least two alkali substances can be used in combination. The alkali substance may be added in the form of a solution thereof in a polar solvent. The number (C) of moles of the alkali substance containing an alkali metal, to be added, is in the range of the following formula, $$C/(xB-A) 0.1 \text{ to } 3$$

wherein x represents a valence of the acidic substance.

The alkali substance containing an alkali metal is preferably added in such an amount that, after 4 parts by weight of toluene and 4 parts by weight of pure water are added per 1 part by weight of the solution (b) obtained after the addition of the alkali substance and the mixture is stirred and then left to stand to separate an aqueous solution, the aqueous solution has a pH of 5.2 to 7.0, more preferably 5.5 to 6.5. The alkali substance containing an alkali metal reacts with the acidic substance, to generate a salt. Therefore, a vinyl compound in which the amount of ionic impurities derived from remaining acidic substance is extremely small can be produced by adding the alkali substance containing an alkali metal.

When the alkali substance containing an alkali metal is not added to the solution (a) or when the amount of the alkali substance added is insufficient, a large amount of a hydrolysable halogen remains in the vinyl compound. On the other hand, when the alkali substance containing an alkali metal is added in an excess amount, ionic impurities derived form the alkali substance remains in a large amount.

In the process provided by the present invention, after the vinyl-benzylating reaction, a salt is removed from the solution (a), to which the acidic substance in an specific amount has been added, without carrying out a step of washing an organic layer with pure water or the like, a salt is removed from the solution (b), to which the alkali substance containing an alkali metal in a specific amount has been added, to obtain a filtrate, and the filtrate is mixed with water or a water/alcohol mixed solution, thereby precipitating a solid. Generally, when an organic solvent solution containing an oligomer dissolved therein is washed with water, an emulsion is apt to generate and it is difficult to carry out liquid-liquid separation. Accordingly, a step of liquid-separation/washing takes a very long period of time. Further, even when the liquid-separation/washing is carried out with water, it is also difficult to completely remove a salt generated in a reaction. In the process of the present invention, since the vinyl-benzylating reaction of the bifunctional phenylene ether oligomer is carried out in the non-protonic polar solvent which is water-soluble, it is possible to use water as a poor solvent for solidification and it is also possible to omit such complicated liquid-separation/washing step. Furthermore, it is possible to dissolve and remove a salt generated in the reaction by washing an obtained solid with water, an alcohol or a water/alcohol mixed solution. The alcohol of the water/alcohol mixed solution may be selected from the group consisting of methanol, ethanol, n-propanol and isopropanol. The alcohol may be used singly or at least two alcohols may be used in combination. Owing to the above process, the vinyl compound, which has very extremely small amounts of ionic impurities and remaining alkali metal ions, can be efficiently produced.

EXAMPLES

The present invention will be concretely explained with reference to Examples and Comparative Examples hereinafter, while the present invention shall not be specially limited to these Examples. Measurements were carried out as follows.

1) A number average molecular weight and a weight average molecular weight were obtained by a gel permeation chromatography (GPC) method. Data processing was carried out according to the GPC curve and molecular weight calibration curve of a sample. The molecular weight calibration curve was obtained by making an approximation of a relation between the molecular weight of a standard polystyrene and an elution time with the following equation, $$\mathrm{Log}\, M = A_0 X^3 + A_1 X^3 + A_1 X^2 + A_2 X + A_3 + A_4 / X^2$$

wherein M: a molecular weight, X: an elution time −19 (minute), and A: a coefficient.

2) A hydroxyl group equivalent of a bifunctional phenylene ether oligomer was obtained by acetylating a phenolic hydroxyl group, then neutralizaing and titrating acetic acid derived from an unreacted actylation reagent with sodium hydroxide, and quantifying a consumption of the acetylation reagent.

3) An electrode, Inpro4250SG/225/Pt1000 supplied by METTLER TLED, was used for pH measurement.

Figure 1:
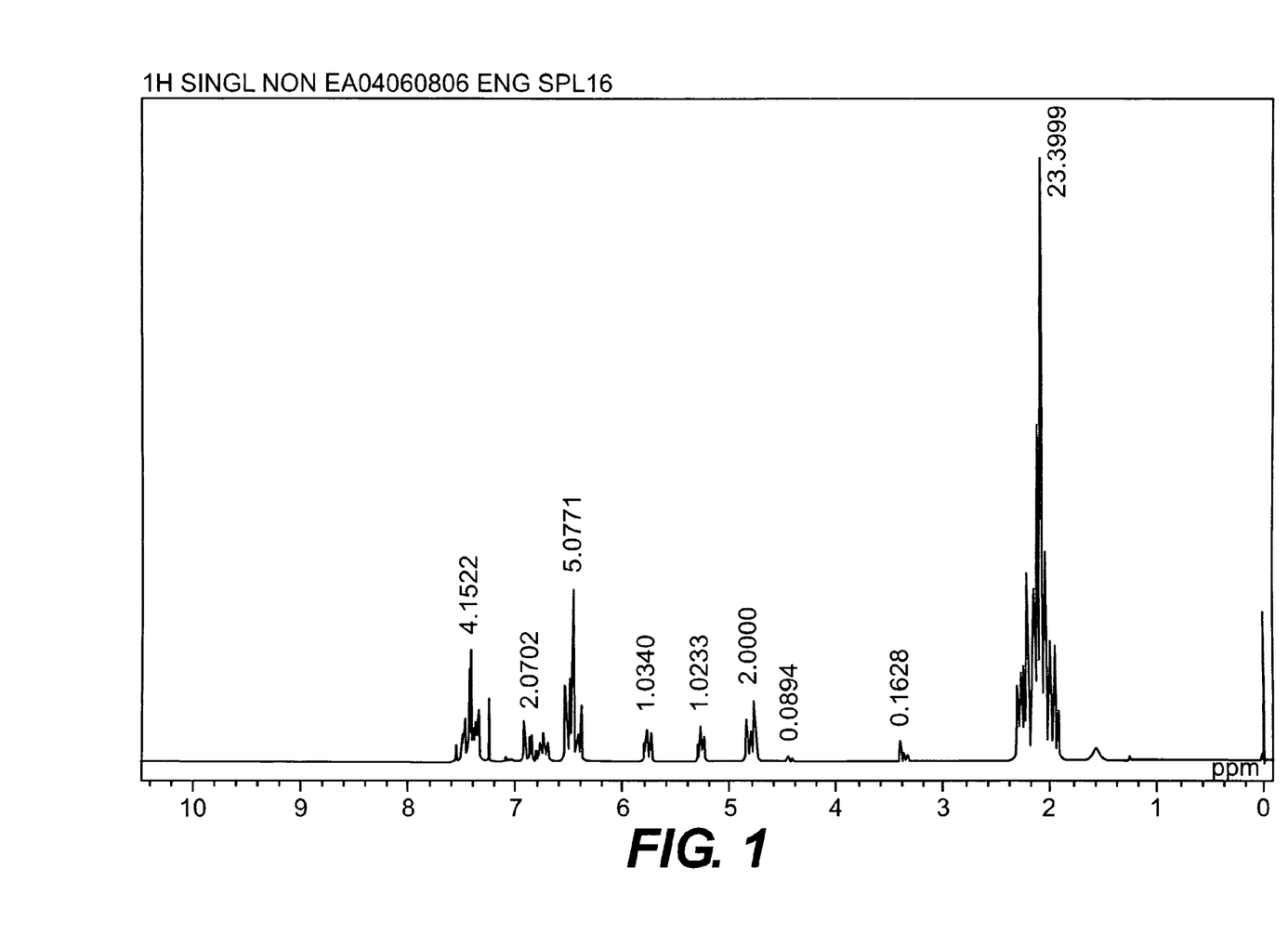
FIG. 1 shows $^1$H-NMR chart of a vinyl compound.
Figure 2:
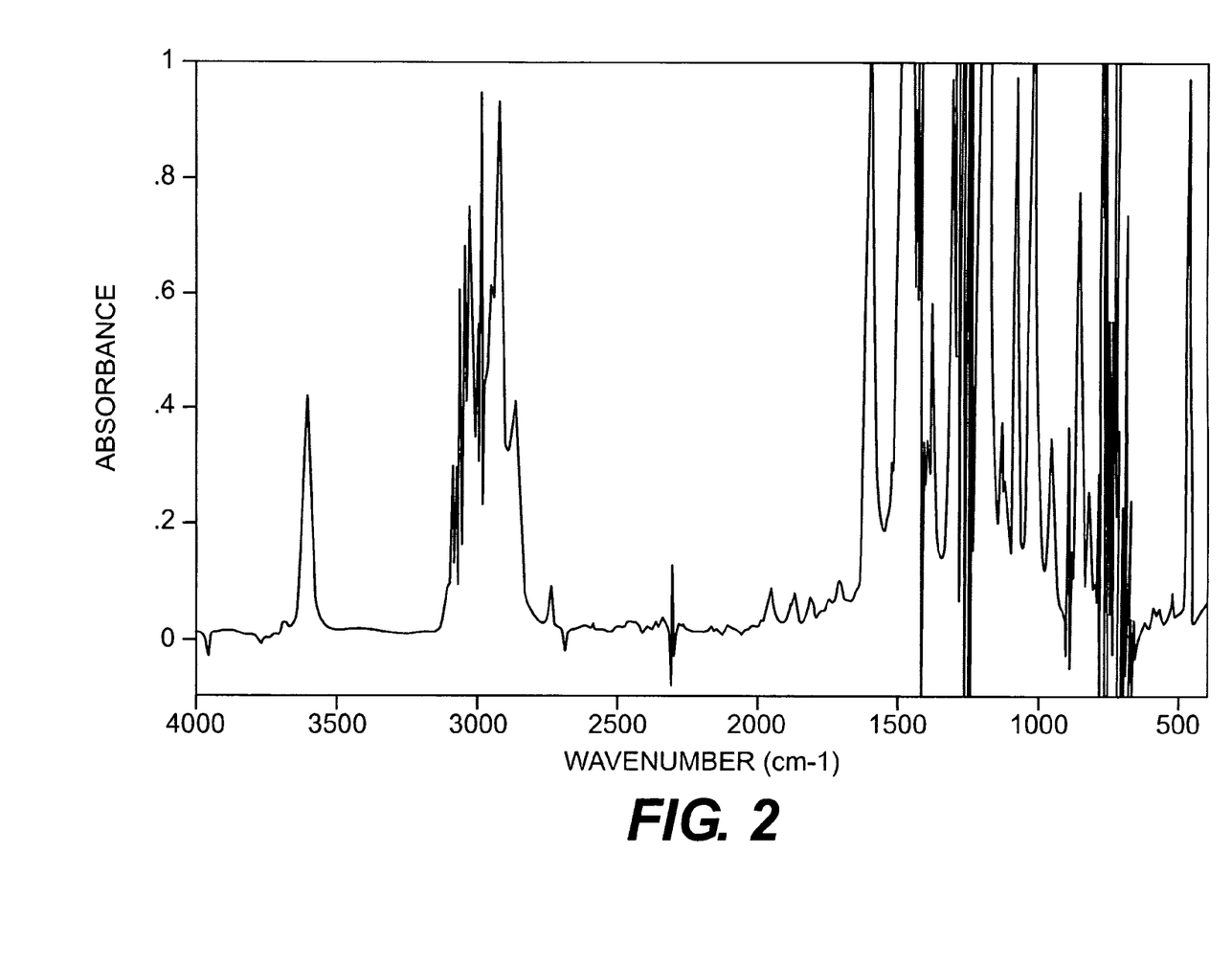
FIG. 2 shows IR chart of a bifunctional phenylene ether oligomer.
Figure 3:
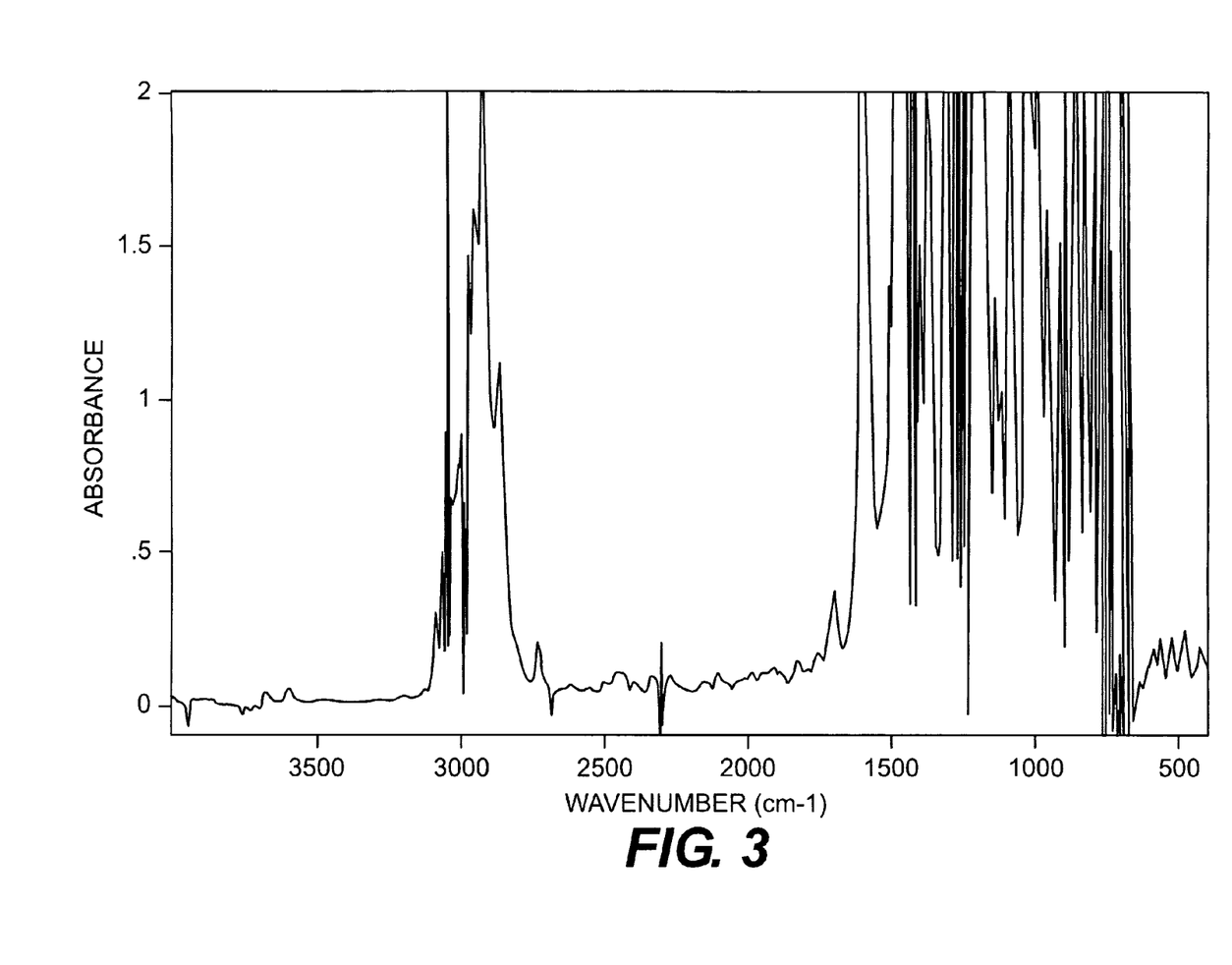
FIG. 3 shows IR chart of a vinyl compound.

4) A vinyl compound was confirmed on the basis of a peak of vinylbenzyl ether in $^1$H-NMR analysis (FIG. 1). Further, it was confirmed that a peak (FIG. 2) of a phenolic hydroxyl group of a bifunctional phenylene ether oligomer disappeared in the vinyl compound (FIG. 3) in an IR analysis.

5) The amount of a hydrolysable halogen was quantified as follows. A vinyl compound was dissolved in dioxane, 0.1N potassium hydroxide methanol solution was added and the resultant mixture was stirred under heat for 15 minutes under a refluxing state. The amount of a halogen which had been eliminated during the stirring was quantified by titration with a silver nitrate aqueous solution. It is represented by weight fraction.

6) The quantitative analysis of a solution was carried out using a gas chromatography (GC-14A; supplied by Shimadzu Corporation) and PEG20M (GL Science) as column packing.

7) A fluorescent x-ray analyzer, RIX3000, (supplied by Rigaku Denki Kogyo K.K.) was used for the analysis of Na.

8) A cured product was measured for a dielectric constant and a dielectric loss tangent by a cavity resonator perturbation method.

Referential Example 1

A longitudinally long reactor having a volume of 400 liters and equipped with a stirrer, a thermometer, an air-introducing tube and baffleplates was charged with 28.38 g (0.127 mol) of $CuBr_2$, 21.89 g (0.127 mol) of N,N'-di-t-butylethylenediamine, 738.86 g (7.30 mol) of n-butyldimethylamine, 70.50 kg of toluene and 2.98 kg of methanol. The mixture was stirred at a reaction temperature of 42° C. Separately, 1,436 g (5.31 mol) of 2,2',3,3',5,5'-hexamethyl-(1,1'-biphenyl)-4,4'-diol (to be referred to as HMBP hereinafter), 9,740 g (79.72 mol) of 2,6-dimethylphenol, 47.43 g (0.212 mmol) of $CuBr_2$, 36.59 g (0.212 mmol) of N,N'-di-t-butylethylenediamine and 195.89 g (1.94 mol) of n-butyldimethylamine were dissolved in a mixed solvent containing 18.7 kg of toluene and 24.6 kg of methanol, to obtain a mixed solution. The mixed solution was dropwise added to the mixture in the reactor over 239 minutes with stirring while bubbling was carried out with a nitrogen-air mixed gas having an oxygen concentration of 8% at a flow velocity of 139 L/min. After the completion of the addition, 40.5 kg of water in which 774 g (1.71 mol) of tetrasodium ethylenediamine tetraacetate was dissolved was added to the stirred mixture to terminate the reaction. An aqueous layer and an organic layer were separated. Then, washing was carried out with pure water, to obtain 84.5 kg of a reaction solution (A) of a bifunctional phenylene ether oligomer. The bifunctional phenylene ether oligomer had a number average molecular weight of 1,990, a weight average molecular weight of 3,730 and a hydroxyl group equivalent of 890.

Referential Example 2

A longitudinally long reactor having a volume of 400 liters and equipped with a stirrer, a thermometer, an air-introducing tube and baffleplates was charged with 27.96 g (0.125 mol) of $CuBr_2$, 32.36 g (0.188 mol) of N,N'-di-t-butylethylenediamine, 344.58 g (3.41 mol) of n-butyldimethylamine, 46.10 kg of toluene and 23.28 kg of methanol. The mixture was stirred at a reaction temperature of 42° C. Separately, 3,592 g (13.28 mol) of HMBP, 8,150 g (66.71 mol) of 2,6-dimethylphenol, 36.45 g (0.163 mmol) of $CuBr_2$, 41.80 g (0.243 mmol) of N,N'-di-t-butylethylenediamine and 445.81 g (4.41 mol) of n-butyldimethylamine were dissolved in a mixed solvent containing 30.2 kg of toluene and 15.35 kg of methanol, to obtain a mixed solution. The mixed solution was dropwise added to the mixture in the reactor over 241 minutes with stirring while bubbling was carried out with a nitrogen-air mixed gas having an oxygen concentration of 8% at a flow velocity of 139 L/min. After the completion of the addition, 38.63 kg of water in which 391.39 g (0.865 mol) of tetrasodium ethylenediamine tetraacetate was dissolved was added to the stirred mixture to terminate the reaction. An aqueous layer and an organic layer were separated. Then, washing was carried out with pure water, to obtain 73.05 kg of a reaction solution (B) of a bifunctional phenylene ether oligomer. The bifunctional phenylene ether oligomer had a number average molecular weight of 980, a weight average molecular weight of 1,650 and a hydroxyl group equivalent of 440.

Referential Example 3

A longitudinally long reactor having a volume of 12 liters and equipped with a stirrer, a thermometer, an air-introducing tube and baffleplates was charged with 1.04 g (4.66 mmol) of $CuBr_2$, 1.20 g (6.98 mmol) of N,N'-di-t-butylethylenediamine, 12.74 g (125.9 mmol) of n-butyldimethylamine, 1,700 g of toluene and 830 g of methanol. The mixture was stirred at a reaction temperature of 40° C. Separately, 109.6 g (0.385 mol) of 4,4'-(1-methylethylidene)bis(2,6-dimethylphenol), 235.5 g (1.93 mol) of 2,6-dimethylphenol, 1.30 g (5.83 mmol) of $CuBr_2$, 1.51 g (8.78 mmol) of N,N'-di-t-butylethylenediamine and 16.03 g (158.4 mmol) of n-butyldimethylamine were dissolved in a mixed solvent containing 1,630 g of toluene and 780 g of methanol, to obtain a mixed solution. The mixed solution was dropwise added to the mixture in the reactor over 240 minutes with stirring while bubbling was carried out with a nitrogen-air mixed gas having an oxygen concentration of 8% at a flow velocity of 5.2 L/min. After the completion of the addition, 1,690 g of water in which 14.38 g (31.78 mmol) of tetrasodium ethylenediamine tetraacetate was dissolved was added to the stirred mixture to terminate the reaction. An aqueous layer and an organic layer were separated. Then, washing was carried out with pure water, to obtain 3,490 g of a reaction solution (C) of a bifunctional phenylene ether oligomer. The bifunctional phenylene ether oligomer had a number average molecular weight of 1,010, a weight average molecular weight of 1,700 and a hydroxyl group equivalent of 480.

Referential Example 4

A longitudinally long reactor having a volume of 12 liters and equipped with a stirrer, a thermometer, an air-introducing tube and baffleplates was charged with 1.04 g (4.66 mmol) of $CuBr_2$, 1.20 g (6.98 mmol) of N,N'-di-t-butylethylenediamine, 12.74 g (125.9 mmol) of n-butyldimethylamine, 1,700 g of toluene and 830 g of methanol. The mixture was stirred at a reaction temperature of 40° C. Separately, 103.95 g (0.385 mol) of HMBP, 162.12 g (1.35 mol) of 2,6-dimethylphenol, 78.74 g (0.58 mol) of 2,3,6-trimethylphenol, 1.30 g (5.83 mmol) of $CuBr_2$, 1.51 g (8.78 mmol) of N,N'-di-t-butylethylenediamine and 16.03 g (158.4 mmol) of n-butyldimethylamine were dissolved in a mixed solvent containing 1,630 g of toluene and 780 g of methanol, to obtain a mixed solution. The mixed solution was dropwise added to the mixture in the reactor over 240 minutes with stirring while bubbling was carried out with a nitrogen-air mixed gas having an oxygen concentration of 8% at a flow velocity of 5.2 L/min. After the completion of the addition, 1,690 g of water in which 14.38 g (31.78 mmol) of tetrasodium ethylenediamine tetraacetate was dissolved was added to the stirred mixture to terminate the reaction. An aqueous layer and an organic layer were separated. Then, washing was carried out with pure water, to obtain 3,530 g of a reaction solution (D) of a bifunctional phenylene ether oligomer. The bifunctional phenylene ether oligomer had a number average molecular weight of 990, a weight average molecular weight of 1,680 and a hydroxyl group equivalent of 450.

Example 1

64.95 kg of toluene was distilled off from 84.5 kg of the reaction solution (A) obtained in Referential Example 1 under a reduced pressure with heating the reaction solution (A) at 40° C. Then, 75.0 kg of N,N-dimethylacetamide was added to the solution. Then, distillation was again carried out under a reduced pressure under heat at 80° C., to obtain 47.8 kg of a bifunctional phenylene ether oligomer solution (A') containing 77.42 wt % of N,N-dimethylacetamide and 0.02 wt % of toluene. Then, 442.8 g (0.112 mol as OH equivalent) of the bifunctional phenylene ether oligomer solution (A'), 21.3 g (0.140 mol) of vinylbenzyl chloride (p-vinylbenzylchloride:m-vinylbenzylchloride=1:1, trade name CMS-P, supplied by Seimi Chemical Co., Ltd.) and 46.0 g of N,N-dimethylacetamide were added to a reactor equipped with a stirrer, a thermometer and a reflux tube. The mixture was stirred under heat at 50° C. 26.77 g (0.140 mol) of a sodium methoxide methanol solution (concentration: 28.2 wt %) was dropwise added to the reactor with keeping the reaction temperature of 50° C., and the mixture was stirred for 1 hour. Further, 2.23 g (0.012 mol) of a sodium methoxide methanol solution (concentration: 28.2 wt %) was dropwise added. The mixture was heated to 70° C. and stirred for 1 hour. Then, 4.99 g (0.015 mol) of an N,N-dimethylacetamide solution (concentration: 30.0 wt %) of phosphoric acid was added to the stirred mixture. 3 g of the resultant reaction solution was measured out, 12 g of toluene and 12 g of pure water were added to the reaction solution and the mixture was stirred. The stirred mixture was left to stand, to separate an aqueous phase. The aqueous phase had a pH of 4.0. A salt generated was removed by filtration. The period of time required for the salt removal by filtration was 2 minutes. 1.36 g (0.0071 mol) of a sodium methoxide methanol solution (concentration: 28.2 wt %) was dropwise added to the acidic solution from which the salt had been removed. 3 g of the solution after completion of the addition was measured out, 12 g of toluene and 12 g of pure water were added to the solution and the mixture was stirred. The stirred mixture was left to stand, to separate an aqueous phase. The aqueous phase had a pH of 5.8. A salt generated by the addition of the above alkali substance was removed. Then, the resultant solution was dropped into 454 g of water to obtain a solid. A solid-liquid separation was carried out by filtration operation to recover the solid. The solid was washed with 3,600 g of methanol and then dried under a reduced pressure, thereby obtaining 106.1 g of an intended vinyl compound (yield 94%). The vinyl compound had a number average molecular weight of 2,390, a weight average molecular weight of 3,890 and a hydrolysable halogen amount of 40 ppm. Unreacted chloromethylstyrene and remaining Na were not detected. The above vinyl compound was molten, degassed and molded at 150° C. and cured at 200° C. for 3 hours, thereby obtaining a cured product. The cured product was measured for dielectric characteristics. Table 1 shows the results thereof.

Example 2

442.9 g (0.112 mol as OH equivalent) of the bifunctional phenylene ether oligomer solution (A') obtained in Example 1, 21.6 g (0.142 mol) of vinylbenzyl chloride (p-vinylbenzyl-chloride:m-vinylbenzylchloride=1:1, trade name CMS-P, supplied by Seimi Chemical Co., Ltd.) and 57.0 g of N,N-dimethylacetamide were added to a reactor equipped with a stirrer, a thermometer and a reflux tube. The mixture was stirred under heat at 50° C. 35.32 g (0.142 mol) of a potassium methoxide methanol solution (concentration: 28.1 wt %) was dropwise added to the reactor with keeping the reaction temperature of 50° C., and the mixture was stirred for 1 hour. Then, 2.92 g (0.012 mol) of a potassium methoxide methanol solution (concentration: 28.1 wt %) was dropwise added. The mixture was heated to 70° C. and stirred for 1 hour. Then, 5.02 g (0.015 mol) of an N,N-dimethylacetamide solution (concentration: 30.0 wt %) of phosphoric acid was added to the stirred mixture. 3 g of the resultant reaction solution was measured out, 12 g of toluene and 12 g of pure water were added to the reaction solution and the mixture was stirred. The stirred mixture was left to stand, separate an aqueous phase. The aqueous phase had a pH of 3.5. A salt generated was removed by filtration. The period of time required for the salt removal by filtration was 3 minutes. 1.35 g (0.0054 mol) of a potassium methoxide methanol solution (concentration: 28.1 wt %) was dropwise added to the acidic solution from which the salt had been removed. 3 g of the solution after completion of the addition was measured out, 12 g of toluene and 12 g of pure water were added to the solution and the mixture was stirred. The stirred mixture was left to stand, to separate an aqueous phase. The aqueous phase had a pH of 5.5. A salt generated by the addition of the above alkali substance was removed. Then, the resultant solution was dropped into 450 g of water to obtain a solid. A solid-liquid separation was carried out by filtration operation, to recover the solid. The solid was washed with 3,600 g of methanol and 1,000 g of pure water and then dried under a reduced pressure, thereby obtaining 105.0 g of an intended vinyl compound (yield 93%). The vinyl compound had a number average molecular weight of 2,360, a weight average molecular weight of 3,860 and a hydrolysable halogen amount of 30 ppm. Unreacted chloromethylstyrene and remaining Na were not detected. The above vinyl compound was molten, degassed and molded at 150° C. and cured at 200° C. for 3 hours, thereby obtaining a cured product. The cured product was measured for dielectric characteristics. Table 1 shows the results thereof.

Example 3

1,120 g of toluene was distilled off from 1,640 g of the reaction solution (B) obtained in Referential Example 2 under a reduced pressure with heating the reaction solution (B) at 40° C. Then, 1,240 g of N,N-dimethylacetamide was added to the solution. Then, distillation was again carried out under a reduced pressure under heat at 80° C., to obtain 991 g of a bifunctional phenylene ether oligomer solution (B') containing 75.0 wt % of N,N-dimethylacetamide and 0.22 wt % of toluene. Then, 400.0 g (0.224 mol as OH equivalent) of the bifunctional phenylene ether oligomer solution (B'), 41.8 g (0.274 mol) of vinylbenzyl chloride (p-vinylbenzylchloride: m-vinylbenzylchloride=1:1, trade name CMS-P, supplied by Seimi Chemical Co., Ltd.) and 100.0 g of N,N-dimethylacetamide were added to a reactor equipped with a stirrer, a thermometer and a reflux tube. The mixture was stirred under heat at 50° C. 52.33 g (0.274 mol) of a sodium methoxide methanol solution (concentration: 28.3 wt %) was dropwise added to the reactor with keeping the reaction temperature of 50° C., and the mixture was stirred for 1 hour. Further, 4.77 g (0.025 mol) of a sodium methoxide methanol solution (concentration: 28.3 wt %) was dropwise added. The mixture was heated to 60° C. and stirred for 1 hour. Then, 9.78 g (0.030 mol) of an N,N-dimethylacetamide solution (concentration: 30.0 wt %) of phosphoric acid was added to the stirred mixture. 3 g of the resultant reaction solution was measured out, 12 g of toluene and 12 g of pure water were added to the above reaction solution and the mixture was stirred. The stirred mixture was left to stand, to obtain an aqueous phase. The aqueous phase had a pH of 4.6. A salt generated was removed by filtration. The period of time required for the salt removal by filtration was 1 minute. 2.04 g (0.011 mol) of a sodium methoxide methanol solution (concentration: 28.3 wt %) was dropwise added to the acidic solution from which the salt had been removed. 3 g of the solution after completion of the addition was measured out, 12 g of toluene and 12 g of pure water were added to the solution and the mixture was stirred. The stirred mixture was left to stand, to separate an aqueous phase. The aqueous phase had a pH of 5.7. A salt generated by the addition of the above alkali substance was removed. Then, the resultant solution was dropped into 452 g of water to obtain a solid. A solid-liquid separation was carried out by filtration operation to recover the solid. The solid was washed with 2,400 g of methanol and 1,000 g of pure water and then dried under a reduced pressure, thereby obtaining 116.3 g of an intended vinyl compound (yield 92%). The vinyl compound had a number average molecular weight of 1,240, a weight average molecular weight of 1,780 and a hydrolysable halogen amount of 40 ppm. Unreacted chloromethylstyrene and remaining Na were not detected. The above vinyl compound was molten, degassed and molded at 150° C. and cured at 200° C. for 3 hours, thereby obtaining a cured product. The cured product was measured for dielectric characteristics. Table 1 shows the results thereof.

Example 4

400.0 g (0.224 mol as OH equivalent) of the bifunctional phenylene ether oligomer solution (B') obtained in Example 3, 41.8 g (0.274 mol) of vinylbenzyl chloride (p-vinylbenzyl-chloride:m-vinylbenzylchloride=1:1, trade name CMS-P, supplied by Seimi Chemical Co., Ltd.) and 100.0 g of N,N-dimethylacetamide were added to a reactor equipped with a stirrer, a thermometer and a reflux tube. The mixture was stirred under heat at 50° C. 52.34 g (0.274 mol) of a sodium methoxide methanol solution (concentration: 28.3 wt %) was dropwise added to the reactor with keeping the reaction temperature of 50° C., and the mixture was stirred for 1 hour. Then, 4.76 g (0.025 mol) of a sodium methoxide methanol solution (concentration: 28.3 wt %) was dropwise added. The mixture was heated to 60° C. and stirred for 1 hour. Then, 9.87 g (0.030 mol) of an N,N-dimethylacetamide solution (concentration: 29.7 wt %) of phosphoric acid was added to the stirred mixture. 3 g of the resultant reaction solution was measured out, 12 g of toluene and 12 g of pure water were added to the reaction solution and the mixture was stirred. The stirred mixture was left to stand, to separate an aqueous phase. The aqueous phase had a pH of 4.4. A salt generated was removed by filtration. The period of time required for the salt removal by filtration was 2 minutes. 2.19 g (0.012 mol) of a sodium methoxide methanol solution (concentration: 28.3 wt %) was dropwise added to the acidic solution from which the salt had been removed. 3 g of the solution after completion of the addition was measured out, 12 g of toluene and 12 g of pure water were added to the solution and the mixture was stirred. The stirred mixture was left to stand, to separate an aqueous phase. The aqueous phase had a pH of 5.9. A salt generated by the addition of the above alkali substance was removed. Then, the resultant solution was dropped into a mixed solution containing 230 g of water and 230 g of methanol to obtain a solid. A solid-liquid separation was carried out by filtration operation to recover the solid. The solid was washed with 2,400 g of methanol and 1,000 g of pure water and then dried under a reduced pressure, thereby obtaining 113.7 g of an intended vinyl compound (yield 90%). The vinyl compound had a number average molecular weight of 1,270, a weight average molecular weight of 1,820 and a hydrolysable halogen amount of 40 ppm. Unreacted chloromethylstyrene and remaining Na were not detected. The above vinyl compound was molten, degassed and molded at 150° C. and cured at 200° C. for 3 hours, thereby obtaining a cured product. The cured product was measured for dielectric characteristics. Table 1 shows the results thereof.

Example 5

564 g of toluene was distilled off from 766 g of the reaction solution (C) obtained in Referential Example 3 under a reduced pressure with heating the reaction solution (C) at 40° C. Then, 605 g of N,N-dimethylformamide was added to the solution. Then, distillation was again carried out under a reduced pressure under heat at 80° C., to obtain 484 g of a bifunctional phenylene ether oligomer solution (C') containing 75.0 wt % of N,N-dimethylformamide and 0.30 wt % of toluene. Then, 400.0 g (0.208 mol as OH equivalent) of the bifunctional phenylene ether oligomer solution (C'), 36.7 g (0.241 mol) of vinylbenzyl chloride (p-vinylbenzylchloride:m-vinylbenzylchloride=1:1, trade name CMS-P, supplied by Seimi Chemical Co., Ltd.) and 100 g of N,N-dimethylformamide were added to a reactor equipped with a stirrer, a thermometer and a reflux tube. The mixture was stirred under heat at 50° C. 58.04 g (0.241 mol) of a sodium ethoxide ethanol solution (concentration: 28.2 wt %) was dropwise added to the reactor with keeping the reaction temperature of 50° C., and the mixture was stirred for 1 hour. Further, 5.28 g (0.022 mol) of a sodium ethoxide ethanol solution (concentration: 28.2 wt %) was dropwise added. The mixture was heated to 60° C. and stirred for 1 hour. Then, 8.57 g (0.026 mol) of an N,N-dimethylformamide solution (concentration: 30.0 wt %) of phosphoric acid was added to the stirred mixture. 3 g of the resultant reaction solution was measured out, 12 g of toluene and 12 g of pure water were added to the reaction solution and the mixture was stirred. The stirred mixture was left to stand, to separate an aqueous phase. The aqueous phase had a pH of 4.8. A salt generated was removed by filtration. The period of time required for the salt removal by filtration was 2 minutes. 2.63 g (0.011 mol) of a sodium ethoxide ethanol solution (concentration: 28.2 wt %) was dropwise added to the acidic solution from which the salt had been removed. 3 g of the solution after completion of the addition was measured out, 12 g of toluene and 12 g of pure water were added to the solution and the mixture was stirred. The stirred mixture was left to stand, to separate an aqueous phase. The aqueous phase had a pH of 6.1. A salt generated by the addition of the above alkali substance was removed. Then, the resultant solution was dropped into 450 g of water, to obtain a solid. A solid-liquid separation was carried out by filtration operation to recover the solid. The solid was washed with 2,400 g of methanol and 1,000 g of pure water and then dried under a reduced pressure, thereby obtaining 112.9 g of an intended vinyl compound (yield 92%). The vinyl compound had a number average molecular weight of 1,210, a weight average molecular weight of 1,810 and a hydrolysable halogen amount of 50 ppm. Unreacted chloromethylstyrene and remaining Na were not detected. The above vinyl compound was molten, degassed and molded at 150° C. and cured at 200° C. for 3 hours, thereby obtaining a cured product. The cured product was measured for dielectric characteristics. Table 1 shows the results thereof.

Example 6

750 g of toluene was distilled off from 1,026 g of the reaction solution (D) obtained in Referential Example 4 under a reduced pressure with heating the reaction solution (D) at 40° C. Then, 550 g of N-methyl-2-pyrrolidone was added to the solution. Then, distillation was again carried out under a reduced pressure under heat at 80° C., to obtain 480 g of a bifunctional phenylene ether oligomer solution (D') containing 79.2 wt % of N-methyl-2-pyrrolidone and 0.10 wt % of toluene. Then, 480.0 g (0.222 mol as OH equivalent) of the bifunctional phenylene ether oligomer solution (D') and 37.2 g (0.244 mol) of vinylbenzyl chloride (p-vinylbenzylchloride:m-vinylbenzylchloride=1:1, trade name CMS-P, supplied by Seimi Chemical Co., Ltd.) were added to a reactor equipped with a stirrer, a thermometer and a reflux tube. The mixture was stirred under heat at 50° C. 46.72 g (0.244 mol) of a sodium methoxide methanol solution (concentration: 28.2 wt %) was dropwise added to the reactor with keeping the reaction temperature of 50° C., and the mixture was stirred for 1 hour. Further, 1.60 g (0.023 mol) of a sodium methoxide methanol solution (concentration: 28.2 wt %) was dropwise added. The mixture was heated to 60° C. and stirred for 1 hour. Then, 8.57 g (0.026 mol) of an N-methyl-2-pyrrolidone solution (concentration: 30.0 wt %) of phosphoric acid was added to the stirred mixture. 3 g of the resultant reaction solution was measured out, 12 g of toluene and 12 g of pure water were added to the reaction solution and the mixture was stirred. The stirred mixture was left to stand, to separate an aqueous phase. The aqueous phase had a pH of 4.9. A salt generated was removed by filtration. The period of time required for the salt removal by filtration was 2 minutes. 2.63 g (0.011 mol) of a sodium methoxide methanol solution (concentration: 28.2 wt %) was dropwise added to the acidic solution from which the salt had been removed. 3 g of the solution after completion of the addition was measured out, 12 g of toluene and 12 g of pure water were added to the solution and the mixture was stirred. The stirred mixture was left to stand, to separate ad an aqueous phase. The aqueous phase had a pH of 6.3. A salt generated by the addition of the above alkali substance was removed. Then, the resultant solution was dropped into 450 g of water to obtain a solid. A solid-liquid separation was carried out by filtration operation to recover the solid. The solid was washed with 2,400 g of methanol and 1,000 g of pure water and then dried under a reduced pressure, thereby obtaining 116.0 g of an intended vinyl compound (yield 94%). The vinyl compound had a number average molecular weight of 1,280, a weight average molecular weight of 1,860 and a hydrolysable halogen amount of 50 ppm. Unreacted chloromethylstyrene and remaining Na were not detected. The above vinyl compound was molten, degassed and molded at 150° C. and cured at 200° C. for 3 hours, thereby obtaining a cured product. The cured product was measured for dielectric characteristics. Table 1 shows the results thereof.

Example 7

The reaction solution (B) obtained in Referential Example 2 was concentrated with an evaporator and then dried in vacuum at 130° C., to obtain a bifunctional phenylene ether oligomer (B") powder. Then, 100.0 g (0.227 mol as OH equivalent) of the bifunctional phenylene ether oligomer (B") powder and 400.0 g of N,N-dimethylacetamide were added to a reactor equipped with a stirrer, a thermometer and a reflux tube, to obtain a solution. 39.90 g (0.261 mol) of vinylbenzyl chloride (p-vinylbenzylchloride:m-vinylbenzylchloride=1:1, trade name CMS-P, supplied by Seimi Chemical Co., Ltd.) was added to the solution. The mixture was stirred under heat at 50° C. 50.24 g (0.261 mol) of a sodium methoxide methanol solution (concentration: 28.1 wt %) was dropwise added to the reactor with keeping the reaction temperature of 50° C., and the mixture was stirred for 1 hour. Further, 4.57 g (0.024 mol) of a sodium methoxide methanol solution (concentration: 28.1 wt %) was dropwise added. The mixture was heated to 60° C. and stirred for 1 hour. Then, 9.31 g (0.029 mol) of an N,N-dimethylacetamide solution (concentration: 30.0 wt %) of phosphoric acid was added to the stirred mixture. 3 g of the resultant reaction solution was measured out, 12 g of toluene and 12 g of pure water were added to the reaction solution and the mixture was stirred. The stirred mixture was left to stand, to separate an aqueous phase. The aqueous phase had a pH of 4.7. A salt generated was removed by filtration. The period of time required for the salt removal by filtration was 1 minute. 1.61 g (0.0084 mol) of a sodium methoxide methanol solution (concentration: 28.1 wt %) was dropwise added to the acidic solution from which the salt had been removed. 3 g of the solution after completion of the addition was measured out, 12 g of toluene and 12 g of pure water were added to the solution and the mixture was stirred. The stirred mixture was left to stand, to separate an aqueous phase. The aqueous phase had a pH of 5.9. A salt generated by the addition of the above alkali substance was removed. Then, the resultant solution was dropped into 452 g of water to obtain a solid. A solid-liquid separation was carried out by filtration operation to recover the solid. The solid was washed with 2,400 g of methanol and 1,000 g of pure water and then dried under a reduced pressure, thereby obtaining 116.2 g of an intended vinyl compound (yield 92%). The vinyl compound had a number average molecular weight of 1,230, a weight average molecular weight of 1,770 and a hydrolysable halogen amount of 20 ppm. Unreacted chloromethylstyrene and remaining Na were not detected. The above vinyl compound was molten, degassed and molded at 150° C. and cured at 200° C. for 3 hours, thereby obtaining a cured product. The cured product was measured for dielectric characteristics. Table 1 shows the results thereof.

Comparative Example 1

442.9 g (0.112 mol as OH equivalent) of the bifunctional phenylene ether oligomer solution (A') obtained in Example 1, 21.6 g (0.141 mol) of vinylbenzyl chloride (p-vinylbenzyl-chloride:m-vinylbenzylchloride=1:1, trade name CMS-P, supplied by Seimi Chemical Co., Ltd.) and 58.0 g of N,N-dimethylacetamide were added to a reactor equipped with a stirrer, a thermometer and a reflux tube. The mixture was stirred under heat at 50° C. 27.10 g (0.142 mol) of a sodium methoxide methanol solution (concentration: 28.2 wt %) was dropwise added to the reactor with keeping the reaction temperature of 50° C., and the mixture was stirred for 1 hour. Then, 6.76 g (0.035 mol) of a sodium methoxide methanol solution (concentration: 28.2 wt %) was dropwise added. The mixture was heated to 70° C. and stirred for 3 hours. Then, 10.49 g (0.032 mol) of an N,N-dimethylacetamide solution (concentration: 30.0 wt %) of phosphoric acid was added to the stirred mixture. 3 g of the resultant reaction solution was measured out, 12 g of toluene and 12 g of pure water were added to the reaction solution and the mixture was stirred. The stirred mixture was left to stand, to separate an aqueous phase. The aqueous phase had a pH of 5.2. A salt generated was removed by filtration. However, it took 80 minutes to complete the filtration. Then, the resultant reaction solution was dropped into 450 g of water to obtain a solid. A solid-liquid separation was carried out by filtration operation, to recover the solid. The solid was washed with 3,600 g of methanol and then dried under a reduced pressure, thereby obtaining 87.3 g of an intended vinyl compound (yield 87%). The vinyl compound had a number average molecular weight of 2,330, a weight average molecular weight of 3,740 and a hydrolysable halogen amount of 60 ppm. Unreacted chloromethylstyrene and remaining Na were not detected. The above vinyl compound was molten, degassed and molded at 150° C. and cured at 200° C. for 3 hours, thereby obtaining a cured product. The cured product was measured for dielectric characteristics. Table 1 shows the results thereof.

Comparative Example 2

420.0 g (0.237 mol as OH equivalent) of the bifunctional phenylene ether oligomer solution (B') obtained in Example 3, 41.4 g (0.271 mol) of vinylbenzyl chloride (p-vinylbenzyl-chloride:m-vinylbenzylchloride=1:1, trade name CMS-P, supplied by Seimi Chemical Co., Ltd.) and 80 g of N,N-dimethylacetamide were added to a reactor equipped with a stirrer, a thermometer and a reflux tube. The mixture was stirred under heat at 50° C. 51.89 g (0.271 mol) of a sodium methoxide methanol solution (concentration: 28.2 wt %) was dropwise added to the reactor with keeping the reaction temperature of 50° C., and the mixture was stirred for 1 hour. Further, 8.74 g (0.025 mol) of a sodium methoxide methanol solution (concentration: 28.2 wt %) was dropwise added. The mixture was heated to 60° C. and stirred for 1 hour. Then, 10.80 g (0.033 mol) of an N,N-dimethylacetamide solution (concentration: 30.0 wt %) of phosphoric acid was added to the stirred mixture. 3 g of the resultant reaction solution was measured out, 12 g of toluene and 12 g of pure water were added to the reaction solution and the mixture was stirred. The stirred mixture was left to stand, to separate an aqueous phase. The aqueous phase had a pH of 4.2. A salt generated was removed by filtration. The period of time required for the salt removal by filtration was 4 minutes. The acidic solution, from which the salt had been removed, was dropped into 450 g of water to obtain a solid. A solid-liquid separation was carried out by filtration operation, to recover the solid. The solid was washed with 2,400 g of methanol and 1,000 g of pure water and then dried under a reduced pressure, thereby obtaining 115.7 g of an intended vinyl compound (yield 88%). The vinyl compound had a number average molecular weight of 1,270, a weight average molecular weight of 1,820 and a hydrolysable halogen amount of 210 ppm. Unreacted chloromethylstyrene and remaining Na were not detected. The above vinyl compound was molten, degassed and molded at 150° C. and cured at 200° C. for 3 hours, thereby obtaining a cured product. The cured product was measured for dielectric characteristics. Table 1 shows the results thereof.

Comparative Example 3

443.2 g (0.112 mol as OH equivalent) of the bifunctional phenylene ether oligomer solution (A') obtained in Example 1, 21.4 g (0.140 mol) of vinylbenzyl chloride (p-vinylbenzyl-chloride:m-vinylbenzylchloride=1:1, trade name CMS-P, supplied by Seimi Chemical Co., Ltd.) and 40 g of N,N-dimethylacetamide were added to a reactor equipped with a stirrer, a thermometer and a reflux tube. The mixture was stirred under heat at 50° C. 26.8 g (0.140 mol) of a sodium methoxide methanol solution (concentration: 28.2 wt %) was dropwise added to the reactor with keeping the reaction temperature of 50° C., and the mixture was stirred for 1 hour. Further, 2.23 g (0.012 mol) of a sodium methoxide methanol solution (concentration: 28.2 wt %) was dropwise added. The mixture was heated to 70° C. and stirred for 1 hour. Then, 5.09 g (0.015 mol) of an N,N-dimethylacetamide solution (concentration: 29.5 wt %) of phosphoric acid was added to the stirred mixture. 3 g of the resultant reaction solution was measured out, 12 g of toluene and 12 g of pure water were added to the reaction solution and the mixture was stirred. The stirred mixture was left to stand, to separate an aqueous phase. The aqueous phase had a pH of 4.1. A salt generated was removed by filtration. The period of time required for the salt removal by filtration was 2 minutes. 2.46 g (0.013 mol) of a sodium methoxide methanol solution (concentration: 28.2 wt %) was dropwise added to the acidic solution from which the salt had been removed. 3 g of the solution after completion of the addition was measured out, 12 g of toluene and 12 g of pure water were added to the solution and the mixture was stirred. The stirred mixture was left to stand, to separate an aqueous phase. The aqueous phase had a pH of 7.2. A salt generated by the addition of the above alkali substance was removed. Then, the resultant solution was dropped into 480 g of water to obtain a solid. A solid-liquid separation was carried out by filtration operation, to recover the solid. The solid was washed with 3,600 g of methanol and 1,000 g of pure water and then dried under a reduced pressure, thereby obtaining 104.0 g of an intended vinyl compound (yield 92%). The vinyl compound had a number average molecular weight of 2,340, a weight average molecular weight of 3,800 and a hydrolysable halogen amount of 30 ppm. Unreacted chloromethylstyrene was not detected but 80 ppm of remaining Na was detected. The above vinyl compound was molten, degassed and molded at 150° C. and cured at 200° C. for 3 hours, thereby obtaining a cured product. The cured product was measured for dielectric characteristics. Table 1 shows the results thereof.

TABLE 1

| | | Ex. 1 | Ex. 2 | Ex. 3 | Ex. 4 | Ex. 5 |
|---|---|---|---|---|---|---|
| Synthesis conditions | Reaction time (h) | 2 | 2 | 2 | 2 | 2 |
| | Reaction solvent | DMAC | DMAC | DMAC | DMAC | DMF |
| | CMS amount(mol) | 0.140 | 0.142 | 0.274 | 0.274 | 0.241 |
| | Alkoxide | NaOMe | KOMe | NaOMe | NaOMe | NaOEt |
| | Amount of Alkoxide (mol) | 0.152 | 0.154 | 0.299 | 0.299 | 0.263 |
| | Amount of Alkoxide-CMS (mol): A | 0.012 | 0.012 | 0.025 | 0.025 | 0.022 |
| | Acidic substance | Phosphoric acid | Phosphoric acid | Phosphoric acid | Phosphoric acid | Phosphoric acid |
| | Valence of acidic substance: x | 3 | 3 | 3 | 3 | 3 |
| | Amount of acidic substance(mol)B | 0.015 | 0.015 | 0.030 | 0.030 | 0.026 |
| | B/A | 1.25 | 1.25 | 1.20 | 1.20 | 1.18 |
| | pH after addition of acidic substance *1) | 4.0 | 3.5 | 4.6 | 4.4 | 4.8 |
| | Salt filtration time (minute) | 2 | 3 | 1 | 2 | 2 |
| | xB − A(mol): B − A | 0.033 | 0.033 | 0.065 | 0.065 | 0.056 |
| | Alkali substance containing alkali metal | NaOMe | KOMe | NaOMe | NaOMe | NaOEt |
| | Amount of alkali substance containing alkali metal(mol): C | 0.0071 | 0.0054 | 0.011 | 0.012 | 0.011 |
| | C/(xB − A) | 0.22 | 0.16 | 0.17 | 0.18 | 0.20 |
| | pH after addition of alkalli substance *1) | 5.8 | 5.5 | 5.7 | 5.9 | 6.1 |
| | Poor solvent for solidification | Water | Water | Water | Methanol/water | water |
| | Amount of poor solvent for solidification (pHr) | 450 | 450 | 450 | 500 | 450 |
| Properties of vinyl compound | Mn | 2,390 | 2,360 | 1,240 | 1,270 | 1,210 |
| | Mw | 3,890 | 3,860 | 1,780 | 1,820 | 1,810 |
| | Hydrolysable chlorine (ppm) | 40 | 30 | 40 | 40 | 50 |
| | Na(ppm) | N.D | N.D | N.D | N.D | N.D |

TABLE 1-continued

|  |  |  |  |  |  |  |
|---|---|---|---|---|---|---|
| Curd product | Dielectric constant (10 GHz) | 2.38 | 2.40 | 2.40 | 2.39 | 2.48 |
|  | Dielectric loss tangent (10 GHz) | 0.0016 | 0.0017 | 0.0025 | 0.0024 | 0.0032 |

|  |  | Ex. 6 | Ex. 7 | CEx. 1 | CEx. 2 | CEx. 3 |
|---|---|---|---|---|---|---|
| Synthesis conditions | Reaction time (h) | 2 | 2 | 4 | 2 | 2 |
|  | Reaction solvent | NMP | DMAC | DMAC | DMAC | DMAC |
|  | CMS amount(mol) | 0.244 | 0.261 | 0.141 | 0.271 | 0.140 |
|  | Alkoxide | NaOMe | NaOMe | NaOMe | NaOMe | NaOMe |
|  | Amount of Alkoxide (mol) | 0.267 | 0.285 | 0.177 | 0.296 | 0.152 |
|  | Amount of Alkoxide-CMS (mol): A | 0.023 | 0.024 | 0.036 | 0.025 | 0.012 |
|  | Acidic substance | Phosphoric acid | Phosphoric acid | Phosphoric acid | Phosphoric acid | Phosphoric acid |
|  | Valence of acidic substance: x | 3 | 3 | 3 | 3 | 3 |
|  | Amount of acidic substance(mol)B | 0.026 | 0.029 | 0.032 | 0.033 | 0.015 |
|  | B/A | 1.13 | 1.21 | 0.89 | 1.32 | 1.25 |
|  | pH after addition of acidic substance *1) | 4.9 | 4.7 | 5.2 | 4.2 | 4.1 |
|  | Salt filtration time (minute) | 2 | 1 | 80 | 4 | 2 |
|  | xB − A(mol): B − A | 0.055 | 0.063 | 0.060 | 0.074 | 0.033 |
|  | Alkali substance containing alkali metal | NaOMe | NaOMe | Nil | Nil | NaOMe |
|  | Amount of alkali substance containing alkali metal(mol): C | 0.011 | 0.0084 | 0 | 0 | 0.013 |
|  | C/(xB − A) | 0.20 | 0.13 | 0 | 0 | 0.39 |
|  | pH after addition of alkalli substance *1) | 6.3 | 5.9 | Nil | Nil | 7.2 |
|  | Poor solvent for solidification | Water | Water | Water | Water | Water |
|  | Amount of poor solvent for solidification (pHr) | 450 | 450 | 450 | 450 | 450 |
| Properties of vinyl compound | Mn | 1,280 | 1,230 | 2,330 | 1,270 | 2,340 |
|  | Mw | 1,860 | 1,770 | 3,740 | 1,820 | 3,800 |
|  | Hydrolysable chlorine (ppm) | 50 | 20 | 60 | 210 | 30 |
|  | Na(ppm) | N.D | N.D | N.D | N.D | 80 |
| Curd product | Dielectric constant (10 GHz) | 2.41 | 2.40 | 2.41 | 2.42 | 2.41 |
|  | Dielectric loss tangent (10 GHz) | 0.0017 | 0.0024 | 0.0017 | 0.0035 | 0.0018 |

Ex. = Example
DMAC: N,N-dimethylacetamide.
DMF: N,N-dimethylformamide.
NMP: N-methyl-2-pyrrolidone.
CMS: Vinylbenzyl chloride (chloromethylstyrene).
N.D.: Not detected.
The amount of poor solvent for solidification: The amount is represented on the basis of 100 phr of bifunctional phenylene ether oligomer.
X: Valence of acidic substance.
*1) pH: pH of an aqueous phase obtained by measuring out 3 g of a reaction solution, adding 12 g of toluene and 12 g of pure water, stirring the mixture and leaving it to stand, to separate the aqueous phase.
Ex. = Example, CEx. = Comparative Example.

What is claimed is:

1. A process for the production of a vinyl compound represented by formula (1), comprising subjecting a non-protonic polar solvent solution of a bifunctional phenylene ether oligomer represented by formula (2) to the steps of:
   1) reacting the bifunctional phenylene ether oligomer of formula (2) with a vinylbenzyl halide in the presence of an alkoxide of an alkali metal in an amount in excess of the number of moles of the vinylbenzyl halide, to synthesize the vinyl compound represented by formula (1),
   2) after the completion of the reaction, adding an acidic substance in such an amount that the number (B) of moles of the acidic substance is at least 1.0 molar times as much as a difference (A) between the number of moles of the vinylbenzyl halide and the number of moles of the alkali metal of the alkoxide, to obtain a solution (a) and removing a salt precipitated in the solution (a) by filtration,
   3) adding an alkali substance containing an alkali metal in such an amount that the number (C) of moles of the alkali metal satisfies C/(xB−A)=0.1 to 3, wherein x represents a valence of the acidic substance, to obtain a solution (b), wherein 4 parts by weight of toluene and 4 parts by weight of pure water are added to 1 part by weight of the solution (b) to obtain a mixture, the mixture is stirred and then left to stand, to separate an aqueous phase and the aqueous phase has a pH of 5.2 to 7.0, and removing a salt precipitated in the solution (b) by filtration, to obtain a filtrate, and
   4) mixing the filtrate with water or a mixed solution containing water and an alcohol, thereby precipitating the vinyl compound represented by formula (1),

(1)

wherein $R^1$, $R^2$, $R^3$ and $R^4$ are the same or different and represent a hydrogen atom, a halogen atom, an alkyl group or a phenyl group, —(O—X—O)— represents a moiety of formula (3) or formula (4), —(Y—O)— represents an arrangement of a moiety of formula (5) or an arbitrary arrangement of at least two kinds of moieties of formula (5), and each of a and b is an integer of 0 to 30, provided that at least one of a and b is not 0,

(2)

wherein —(O—X—O)— is a moiety of formula (3) or formula (4), —(Y—O)— represents an arrangement of a moiety of formula (5) or an arbitrary arrangement of at least two kinds of moieties of formula (5) and each of a and b is an integer of 0 to 30, provided that at least one of a and b is not 0,

(3)

wherein $R^5$, $R^6$, $R^7$, $R^{11}$ and $R^{12}$ are the same or different and represent a halogen atom, an alkyl group having 6 or less carbon atoms or a phenyl group and $R^8$, $R^9$ and $R^{10}$ are the same or different and represent a hydrogen atom, a halogen atom, an alkyl group having 6 or less carbon atoms or a phenyl group, (4)

wherein $R^{13}$, $R^{14}$, $R^{19}$ and $R^{20}$ are the same or different and represent a halogen atom, an alkyl group having 6 or less carbon atoms or a phenyl group, $R^{15}$, $R^{16}$, $R^{17}$ and $R^{18}$ are the same or different and represent a hydrogen atom, a halogen atom, an alkyl group having 6 or less carbon atoms or a phenyl group and -A- represents a linear, branched or cyclic hydrocarbon having 20 or less carbon atoms, (5)

wherein $R^{21}$ and $R^{22}$ are the same or different and represent a halogen atom, an alkyl group having 6 or less carbon atoms or a phenyl group and $R^{23}$ and $R^{24}$ are the same or different and represent a hydrogen atom, a halogen atom, an alkyl group having 6 or less carbon atoms or a phenyl group.

2. The process according to claim 1, wherein 4 parts by weight of toluene and 4 parts by weight of pure water are added to 1 part by weight of the solution (a) to obtain a mixture, the mixture is stirred and then left to stand, to separate an aqueous phase and the aqueous phase has a pH of 3.0 to 5.0.

3. The process according to claim 1, wherein $R^5$, $R^6$, $R^7$, $R^{11}$ and $R^{12}$ in —(O—X—O)— of formula (3) or $R^{13}$, $R^{14}$, $R^{19}$ or $R^{20}$ in —(O—X—O)— of formula (4) are methyl groups and —(Y—O)— of formula (5) in formula (1) represents an arrangement of a moiety of formula (6) or formula (7) or an arbitrary arrangement of moieties of formula (6) and formula (7)

(6)

(7)

4. The process according to claim 1, wherein the non-protonic polar solvent is at least one member selected from the group consisting of N,N-dimethylformamide, N,N-dimethylacetamide and N-methyl-2-pyrrolidone.

5. The process according to claim 1, wherein the vinylbenzyl halide is at least one member selected from the group consisting of o-vinylbenzyl chloride, m-vinylbenzyl chloride, p-vinylbenzyl chloride, o-vinylbenzyl bromide, m-vinylbenzyl bromide and p-vinylbenzyl bromide.

6. The process according to claim 1, wherein the alkoxide of the alkali metal is at least one member selected from the group consisting of lithium methoxide, sodium methoxide, potassium methoxide, lithium ethoxide, sodium ethoxide and potassium ethoxide.

7. The process according to claim 1, wherein the acidic substance is at least one member selected from the group consisting of phosphoric acid, sulfuric acid, hydrochloric acid, aromatic sulfonic acid and aromatic carboxylic acid.

8. The process according to claim 1, wherein the alkali substance is at least one member selected from the group consisting of lithium methoxide, sodium methoxide, potassium methoxide, lithium ethoxide, sodium ethoxide, potassium ethoxide, lithium hydroxide, sodium hydroxide and potassium hydroxide.

9. The process according to claim 1, wherein the alcohol is at least one member selected from the group consisting of methanol, ethanol, propanol and isopropanol.

* * * * *